United States Patent [19]

Schroeder et al.

[11] 4,183,853
[45] Jan. 15, 1980

[54] 1-[p-(2-TRIALKYLAMMONIUM)PROPYL-SULFONYLPHENYL]-3-(PHENYL)-PYRAZOLINE SALTS

[75] Inventors: Josef Schroeder, Leverkusen; Carl-Wolfgang Schellhammer, Bergisch-Gladbach, both of Fed. Rep. of Germany

[73] Assignee: Bayer Aktiengesellschaft, Leverkusen, Fed. Rep. of Germany

[21] Appl. No.: 868,317

[22] Filed: Jan. 10, 1978

[30] Foreign Application Priority Data

Jan. 12, 1977 [DE] Fed. Rep. of Germany ....... 2700996

[51] Int. Cl.² .................................. C07D 231/06
[52] U.S. Cl. .......................... 260/239.65; 260/239.9; 252/301.27
[58] Field of Search ..................... 260/239.9, 239.65; 548/379

[56] References Cited

U.S. PATENT DOCUMENTS 3,139,079  4/1964  Wagner et al. .................. 260/239.9

OTHER PUBLICATIONS

Passedouet et al., Chem. Abst. 1970, vol. 72, No. 55447t.
Burger, Medicinal Chemistry, 2nd Ed. Interscience, N.Y. 1960, p. 497.

Primary Examiner—Alan L. Rotman
Assistant Examiner—Natalia Harkaway
Attorney, Agent, or Firm—Sprung, Felfe, Horn, Lynch & Kramer

[57] ABSTRACT

Pyrazoline compounds of the formula

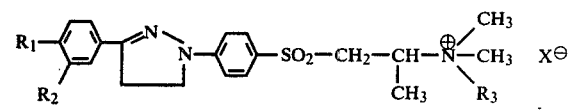

wherein
$R_1$ and $R_2$ denote hydrogen or chlorine,
$R_3$ denotes $C_1$–$C_4$-alkyl and
$X^\ominus$ denotes a colorless anion, are suitable for the whitening of polyacrylonitrile and wool.

1 Claim, No Drawings

1-[P-(2-TRIALKYLAMMONIUM)PROPYLSULFONYLPHENYL]-3-(PHENYL)-PYRAZOLINE SALTS

The invention relates to new pyrazolines, processes for their preparation and their use as whiteners.

It is known (U.S. Pat. No. 3,131,079) that pyrazoline whiteners which contain a trialkylammonium group bonded via an ethylsulphonyl radical are easily accessible and are oustandingly suitable for whitening polyacrylonitrile textile fibres. However, these compounds have the disadvantage that they decompose on storing for relatively long periods, in particular in aqueous solution or under elevated temperature, with the splitting off of the trialkylammonium group.

It has now been found that pyrazoline brighteners of the formula $$R_1 \text{-} \text{Ar}(R_2) \text{-pyrazoline-} \text{Ar} \text{-} SO_2\text{-}CH_2\text{-}CH(CH_3)\text{-}N^{\oplus}(CH_3)_2 R_3 \quad X^{\ominus} \quad (I)$$

wherein $R_1$ and $R_2$ denote hydrogen or chlorine, $R_3$ denotes $C_1$-$C_4$-alkyl and $X^{\ominus}$ denotes a colourless anion, whilst having colouristic properties which are equally good, surprisingly do not exhibit this disadvantage.

The pyrazoline compounds according to the invention can be prepared in the customary manner by reacting ketones of the formula $$R_1 \text{-} \text{Ar}(R_2) \text{-} C(=O)\text{-}CH_2\text{-}CH_2\text{-}Y \quad (II)$$

with hydrazines of the formula $$H_2N\text{-}NH\text{-}\text{Ar}\text{-}SO_2\text{-}CH_2\text{-}CH=CH_2 \quad (III)$$

wherein $R_1$ and $R_2$ have the abovementioned meaning and

Y represents a halogen atom, a di-$C_1$-$C_4$-alkylamino group or a morpholino or piperidino radical, with subsequent reaction of the products with dimethylamine and an alkylating agent. It is particularly advantageous to react the compounds of the formula (II) with the hydrazones of the formula $$(CH_3)_2C=N\text{-}NH\text{-}\text{Ar}\text{-}SO_2\text{-}CH_2\text{-}CH=CH_2 \quad (IV)$$

since it has been shown that the hydrazines of the formula (III) already exhibit decomposition phenomena during their preparation and isolation and cannot be stored for a relatively long period.

On the other hand, the hydrazones of the formula (IV) are stable and can be obtained in a simple manner by adding acetone to the reaction mixture obtained during the preparation of the hydrazines of the formula (III) and lowering the pH to the neutral range.

This course of reaction for preparing the pyrazolines is surprising, since it is known from the literature that hydrazones of aliphatic ketones are more stable than hydrazones of aliphatic-aromatic ketones, and thus a reaction of the hydrazones of the formula (IV) with the ketones of the formula (II), with the splitting off of acetone and HY, could not be expected (L. F. Fieser and M. Fieser, Advanced Organic Chemistry, Reinhold Publishing Corp. New York, 1961, page 417).

In detail, the reaction is carried out by reacting the solution or suspension of the hydrazone (IV) in water, a water-miscible organic solvent or a mixture of water and a water-miscible organic solvent with the ketone (II) at temperatures between 60° and 150° C., depending on the nature of the solvent. The ketone (II) is preferably added dissolved in an organic solvent, for example in a chlorobenzene solution.

Suitable water-miscible solvents are for example, alcohols, ethers and acids, in particular lower aliphatic alcohols, glycols and their partial esters and ethers as well as acetic acid.

Suitable anions $X^{\ominus}$ are, for example, halide ions, such as $Cl^{\ominus}$, $Br^{\ominus}$ or $I^{\ominus}$, $CH_3OSO_3^{\ominus}$, $C_2H_5OSO_3^{\ominus}$, benzenesulphonate and toluenesulphonate.

Appropriately, alkylating agents which are employed are, for example, methyl iodide, dimethyl sulphate, diethyl sulphate and p-toluenesulphonic acid methyl ester.

The new compound are outstandingly suitable for whitening polyacrylonitrile and wool.

EXAMPLE 1

Acetone-(p-allylsulphonylphenyl)-hydrazone 121 g of p-allylsulphonyacetanilide are heated under reflux in 360 ml of dilute hydrochloric acid (2 parts of water, 1 part of concentrated hydrochloric acid) for 2 hours. 250 g of ice are then added and the mixture is cooled to 0° C. After adding a further 125 g of ice, the mixture is diazotised with 35.5 g of sodium nitrite, dissolved in 50 ml of water. The diazonium salt solution is added dropwise at 0° to 5° C. into a sodium bisulphite solution (about 150 g of NaHSO₃), adjusted to pH 6, the pH being maintained at 6 with sodium hydroxide solution. After the reduction, the mixture is warmed to 60° to 80° C. and, after adding 200 ml of concentrated hydrochloric acid, is stirred for 4 hours at 90° C. Active charcoal is then added, the mixture is filtered and the filtrate is cooled and, after adding 110 ml of acetone, is adjusted to pH 6 to 7 with sodium hydroxide solution. The product which has precipitated is filtered off, washed with water and dried. 115 g of acetone-(p-allylsulphonylphenyl)-hydrazone of melting point 105° to 108° C. are obtained.

EXAMPLE 2

1-(p-Allylsulphonylphenyl)-3-(p-chlorophenyl)-pyrazoline 126 g of the product obtained according to Example 1 are dissolved in a mixture of methylglycol and water (80:40) at 90° to 100° C. After adding 1 ml of concentrated hydrochloric acid, a chlorobenzene solution of p,β-dichloropropiophenone (100 g in a total solution of 200 ml) is added dropwise and the mixture is stirred for 6 hours at 100° C. 100 ml of isopropanol are then added and the crystalline product is filtered off. 135 g of 1-(p-allylsulphonylphenyl)-3-(p-chlorophenyl)-pyrazoline of melting point 210° C. are obtained.

1-(p-Allylsulphonylphenyl)-3-(3,4-dichlorophenyl)-pyrazoline of melting point 198° C. is obtained in an analogous manner.

EXAMPLE 3

1-[p-(2-Dimethylamino)-propylsulphonylphenyl]-3-(p-chlorophenyl)-pyrazoline.

360 g of the product obtained according to Example 2, first paragraph, in 300 ml of dimethylformamide are heated to 100° C. with 100 ml of footed dimethylamine in an autoclave. After the reaction has ended, 300 ml of methanol are added and the precipitate which has separated out is filtered off at room temperature, washed with acetone and methanol and then dried. 370 g of 1-[p-(2-dimethylamino)-propylsulphonylphenyl]-3-(p-chlorophenyl)-pyrazoline of melting point 161° to 163° C. are obtained.

When an aqueous dimethylamine solution is used, the reaction can also be carried out under normal pressure.

The following compounds are obtained in an analogous manner: 1-[p-(2-dimethylamino)-propylsulphonylphenyl]-3-(3,4-dichlorophenyl)-pyrazoline of melting point 152° C., 1-[p-(2-morpholino)-propylsulphonylphenyl]-3-(p-chlorophenyl)-pyrazoline of melting point 179° C. and 1-[p-(2-piperidino)-propylsulphonylphenyl]-3-(p-chlorophenyl)-pyrazoline of melting point 158° C.

EXAMPLE 4

1-[p-(2-Trimethylammonium)-propylsulphonylphenyl]-3-(p-chlorophenyl)-pyrazoline methosulphate 101 g of the product obtained according to Example 3, first paragraph, are dissolved in 600 ml of hot methyl ethyl ketone, active charcoal is added, the mixture is filtered and 35 g of dimethyl sulphate are added to the filtrate. The desired methosulphate precipitates, is filtered off hot, washed with a little methyl ethyl ketone and dried. 120 g of 1-[p-(2-trimethylammonium)-propylsulphonylphenyl]-3-(p-chlorophenyl)-pyrazoline methosulphate of melting point 200° C. are obtained.

The amino compounds described in Example 3, last paragraph, can also be methylated in an analogous manner.

EXAMPLE 5

Polyacrylonitrile textile fabrics are treated at the boil in a liquor ratio of 1:40 for 30 minutes with a dye liquor which contains 0.3% of the whitener obtained according to Example 4 and 3% of 30% strength acetic acid (both relative to the textile material). After rinsing and drying, a polyacrylonitrile fabric which is brightened very well and brilliantly is obtained.

Correspondingly wool can be brightened very well by customary dyeing processes (liquor ratio 1:40, 60 minutes at 55° C. and addition of 3 g/l of a commercially available wool-bleaching agent).

We claim:
1. A pyrazoline brightening agent of the formula

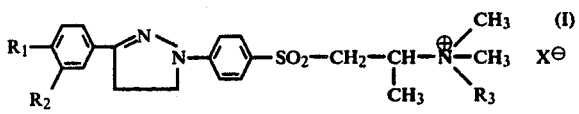

wherein
$R_1$ and $R_2$ denote hydrogen or chlorine,
$R_3$ denotes $C_1$–$C_4$-alkyl and
$X^\ominus$ denotes a colourless anion.

* * * *